United States Patent [19]

James et al.

[11] Patent Number: 4,622,852

[45] Date of Patent: Nov. 18, 1986

[54] GAS MASK FILTERS TEST APPARATUS USING A BREATHING PUMP

[75] Inventors: John T. James, Severn; Leonard C. Buettner, Baltimore; James A. Genovese, Edgewood, all of Md.

[73] Assignee: The United States of America as represented by the Secretary of the Army, Washington, D.C.

[21] Appl. No.: 772,989

[22] Filed: Sep. 6, 1985

[51] Int. Cl.⁴ .............................................. G01N 15/00
[52] U.S. Cl. ................................................... 73/865.6
[58] Field of Search ....... 73/432 DD, 432 PS, 432 R, 73/432 Z, 23; 55/270, 274, DIG. 33

[56] References Cited

U.S. PATENT DOCUMENTS

| | | | |
|---|---|---|---|
| 1,027,823 | 5/1912 | Davis | 73/23 |
| 2,638,688 | 5/1953 | Hazelton | 55/270 |
| 3,328,588 | 6/1967 | Steinberg | 55/270 |
| 3,851,520 | 12/1974 | Schluter et al. | 73/1 G |
| 4,202,212 | 5/1980 | Allen et al. | 55/270 |
| 4,237,726 | 12/1980 | Peterson et al. | 55/270 |

Primary Examiner—Stewart J. Levy
Assistant Examiner—Robert R. Raevis
Attorney, Agent, or Firm—Anthony T. Lane; Robert P. Gibson; Edward F. Costigan

[57] ABSTRACT

A method and apparatus for testing a gas mask filter element comprising, sample supply means for supplying a test sample, a filter element box for containing a gas mask filter element, said element box having a sample inlet connected to said sample means for supplying a test sample to a filter element in the element box to form an effluent in the box, and an effluent outlet for discharging the effluent from the box. An inhalation chamber defining a space and having an effluent inlet connected to said effluent outlet for supplying effluent into said space, said inhalation chamber having a chamber outlet for discharging effluent from said space. At least one plethysmographic box connected to said inhalation chamber for receiving a test animal and having an opening communicating with said space through which the head of a test animal can pass into said inhalation chamber space. Respiration response means connected to said plethysmographic box for measuring a respiratory response of a test animal therein, and a breathing pump connected to said chamber outlet for drawing effluent from said inhalation chamber space in a manner which simulates human respiration.

5 Claims, 8 Drawing Figures

FIG. 3
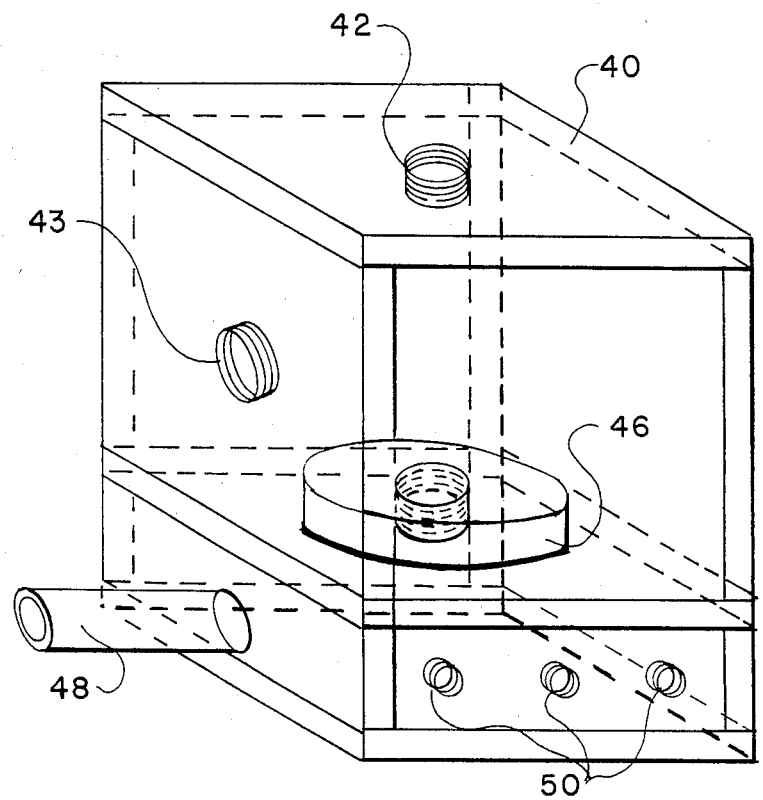
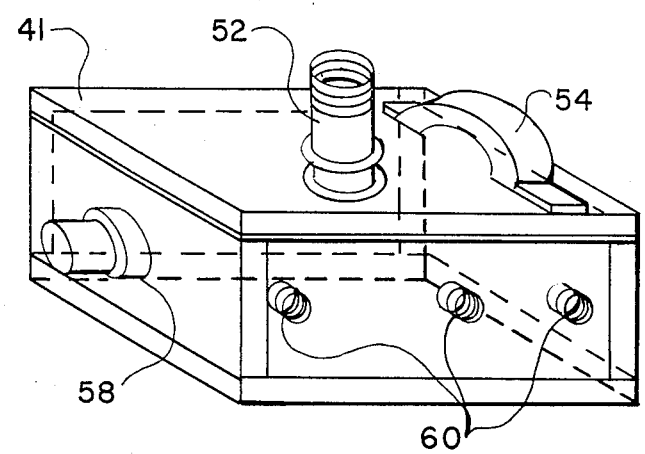
FIG. 4

GAS MASK FILTERS TEST APPARATUS USING A BREATHING PUMP

STATEMENT OF GOVERNMENT INTEREST

The invention described herein may be manufactured, used and licensed by or for the Government for Governmental purposes without the payment to us of any royalties thereon.

FIELD AND BACKGROUND OF THE INVENTION

The present invention relates in general to equipment and methods for testing filters, and in particular to a new and useful apparatus and method for testing a gas mask filter under simulated breathing conditions and using test animals.

The effectiveness of a gas mask filter can be tested using a constant flow apparatus but this does not simulate the variations in pressure to which the filter would actually be exposed under the effects of human respiration. In attempting to reproduce realistic conditions test animals may be used in determining the effectiveness of such filters. Scaled down models of the filters may be used. Some filters however cannot be scaled down effectively. The model M13A2 gas mask filter for example cannot be scaled down using appropriate charcoal.

A way to avoid the use of test animals is to chemically analyze the filter effluent. This however may not detect toxic materials or it may indicate the presence of a compound of unknown toxicity. Consequently, chemical analysis alone may give an incorrect estimate of the protective capacity of the filter.

Even where test animals are utilized, however, toxic signs in testing for the effectiveness of the filter may not demonstrate sensory irritation suffered by the animal.

The apparatus and method of the present invention solves the foregoing problems.

SUMMARY OF THE INVENTION

According to the invention, the challenge (toxic, irritating, etc.) and effluent (filtered) gases are chemically analyzed. At the same time the toxicity of the effluent gases are determined by exposing a test animal to these gases. More realistic test conditions are thus simulated. In addition, rather than supplying the challenge gas in a constant flow to the filter, flow variations which simulate human respiration are utilized. To further simulate human breathing, large diameter passages are utilized which enable an accurate simulation of human respiration during the filter test. The test apparatus is also designed and scaled to accommodate actual filter elements rather than scaled down elements. Test animals in particular rats, are also utilized to test the toxicity and sensory irritation caused by the effluent gas. To this end, the respiratory response of the rats is monitored during the test. This is accomplished by confining the rats in a plethysmographic box and measuring pressure changes (breathing rates and tidal volumes) during exposure. Several advantages are achieved using the present invention. These include an accurate simulation of human respiration using the breath pump. Even without chemical identification of effluent components, reasonably definitive conclusions can be reached concerning filter protection from the animal data. Also very low levels of test vapor in the filter effluent may produce marked toxic signs. Small variations in the composition of the filter affect its ability to protect against certain test vapors and such variations in composition can be determined utilizing the present invention.

Accordingly, an objective of the present invention is to provide an apparatus for testing a gas mask filter element which is comprised of a sample supply means for supplying a test gas or vapor sample, a filter element box for containing the gas mask filter element and having a test sample inlet connected to the sample means for supplying the sample to the filter element which forms an effluent, and an effluent outlet for discharging effluent from the box, an inhalation chamber defining a space and having an effluent inlet connected to the effluent outlet for receiving the effluent into the space, the inhalation chamber having a chamber outlet, at least one plethysmographic box for receiving a laboratory animal and being connected to the inhalation chamber so that the head of the laboratory animal extends into the inhalation chamber, respiratory response means connected to said plethysmographic box for measuring the respiratory response of the test animal in the box, and a breathing pump connected to the chamber outlet of the inhalation chamber for drawing gas from the inhalation chamber and thus for drawing effluent through the effluent inlet in a manner which simulates human respiration.

A further object of the present invention is to provide a gas analyzer which analyzes the challenge gas or vapor, the effluent in the filter element box and the effluent in the inhalation chamber for chemical analysis thereof.

A still further object of the invention is to provide a method for testing the effectiveness of the gas mask filter element utilizing the inventive apparatus.

The various features of novelty which characterize the invention are pointed out with particularity in the claims annexed to and forming a part of the disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a perspective view of a gas mask filter element box for containing a canister type filter element;

FIG. 4 is a view similar to FIG. 3 showing a different embodiment for the filter element box for containing the M13A2 filter element from an M17 type gas mask;

DESCRIPTION OF THE PREFERRED EMBODIMENTS

Figure 1:
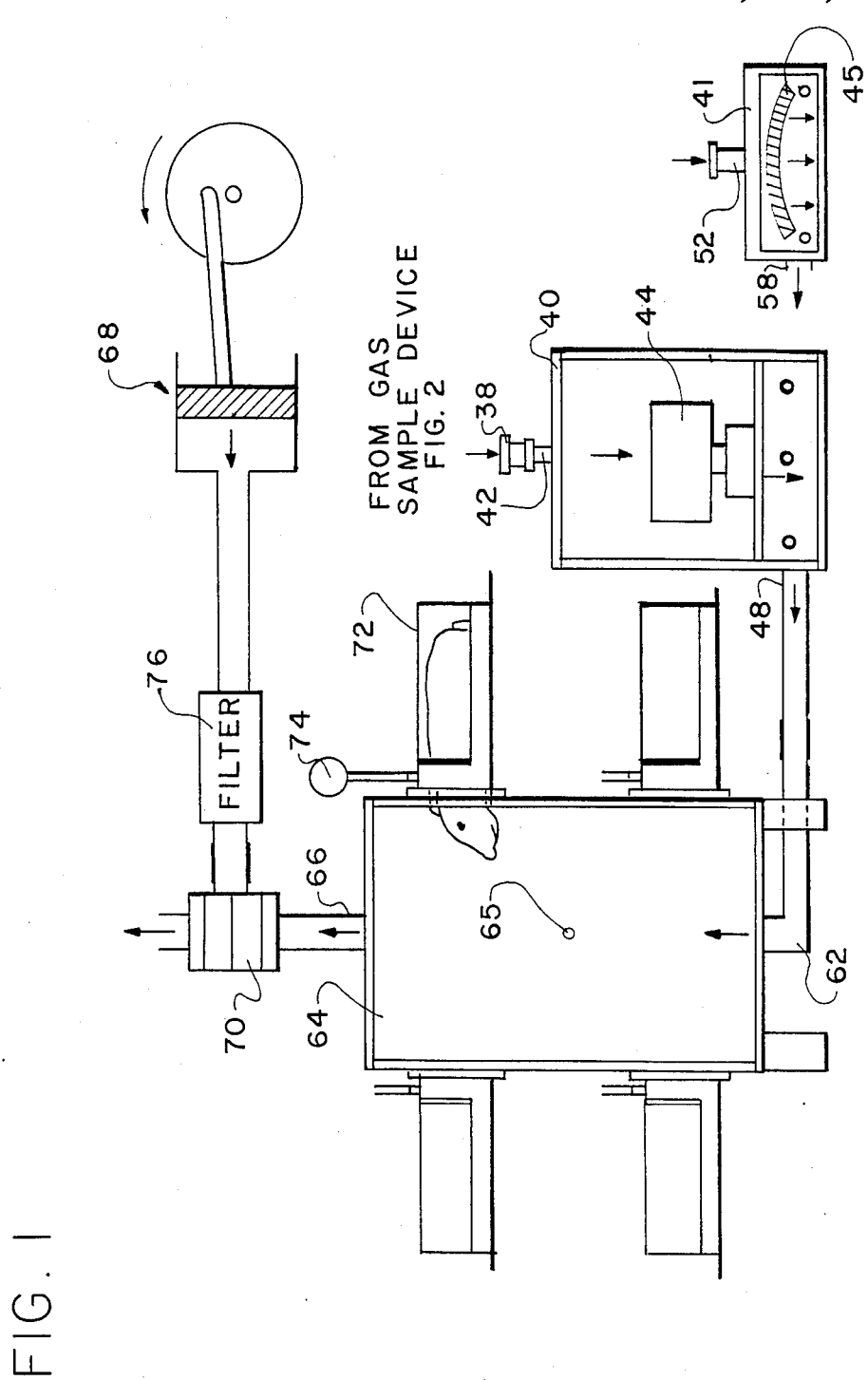
FIG. 1 is a diagram illustrating the filter element box, inhalation chamber and breathing pump in the apparatus of the present invention.
Figure 2:
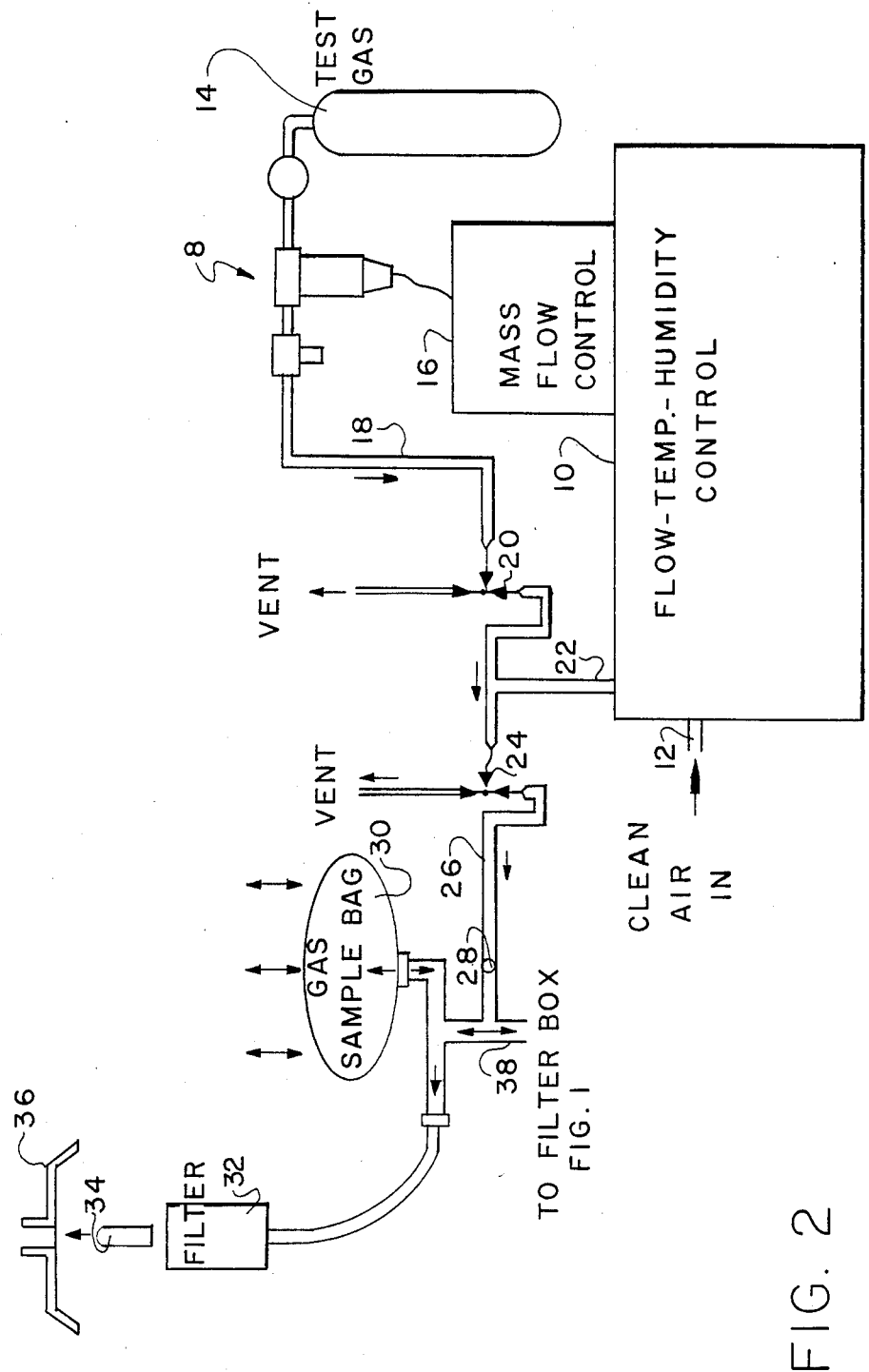
FIG. 2 is a diagram illustrating the apparatus for preparing a gas sample to be filtered by the gas mask filter element.

Referring to the drawings in particular, the invention embodied in FIGS. 1 and 2 comprises an apparatus for testing a gas mask filter element which is mounted in the apparatus of FIG. 1 and which is exposed to a test gas or vapor sample produced by the apparatus of FIG. 2.

In FIG. 2 the methods of sample dissemination, generally designated 8, are provided to produce a test vapor or test gas concentration comprising clean breathing air which is enriched with a controlled amount of test vapor. The sample dissemination means 8 includes a flow-temperature-humidity control system 10 which conditions ambient clean air supplied to the control over an inlet 12, to a specified temperature, flow and relative humidity. Test vapor or gas is supplied from a tank 14 through a mass flow controller 16 and into a test gas line 18. The test gas was supplied into a ball valve 20 to be combined with the preconditioned air in line 22. The mixture of preconditioned air plus test sample was supplied to a second ball valve 24 over a test material sample line 26. Line 26 included a chemical analysis port 28 for drawing a sample from line 26 for chemical analysis. The gas mixture was supplied to a flexible gas sample bag 30 having sufficient capacity to accommodate a breathing machine in the apparatus of FIG. 1, to be described in greater detail later.

Flow is set at 17 liters per minute from which was drawn 16 liters per minute by the breathing pump. Excess flow was passed through a charcoal filter 32 and through a flutter valve 34 to the laboratory fume hood 36 which contained the entire apparatus. The test sample was supplied over line 38 to a filter element box 40 shown in FIG. 1. FIG. 3 shows filter element box 40 in greater detail. Filter element box 40 includes a test gas inlet 42 and is designed to receive a gas mask filter element 44. Filter element 44 is of the canister type such as the model C2 or M11 filter canisters. To accommodate this filter the filter element box includes a threaded canister fitting 46. A second inlet port 43 may also be provided. When line 38 is connected to fitting 42 however fitting 43 is capped.

Filter element box 40 also includes an effluent outlet port 48 for filtered effluent out of box 40. Communicating with port 48 are three chemical analysis ports 50 from which samples of the effluent can be drawn for chemical analysis. During use of the invention, gas chromatographic analysis and IR analysis were utilized to chemically characterize effluent at various points in the equipment and also to analyze the test challenge concentration.

FIGS. 1 and 4 also show an alternate filter element box 41 in which a gas mask filter 45 can be mounted. As with filter element box 40, box 41 includes a test sample inlet 52 and an effluent outlet 58 as well as chemical analysis ports 50. Box 41 also includes a lid with gasket and handle 54.

Either box 40 or box 41 can be connected to the apparatus of FIGS. 1 and 2.

Effluent from box 40 or 41 is supplied to an effluent line 62 which is connected to an input of an inhalation chamber 64. Inhalation chamber 64 includes an effluent outlet 66 which is connected to a breathing pump generally designated 68. The connection is established through a J valve 70 which directs flow from chamber 64 so that "inspired" air is pulled from the inhalation chamber, filter element box, and gas sample bag.

Inhalation chamber 64 includes a chemical analysis port 65 for drawing a sample of effluent for chemical analysis. Connected to chamber 64 are four plethysmographic boxes, one of which is shown at 72. Each box includes an opening communicating with the interior of chamber 64 and having a resilient seal therearound for sealing around the neck of a test animal. Box 72 was dimensioned to receive a 250 to 350 g rat. The respiratory response of the rat was measured using pressure transducers and other equipment shown schematically at 74. A record of this respiration was taken using a two channel strip chart recorder (model 7702B Hewlett-Packard). In practice a laboratory rat was placed in each of the four boxes although only one is shown in FIG. 1.

Breathing pump 68 connected to outlet 66 comprised a motor with a eccentrically connected shaft for actuating a piston in a cylinder. The simulated breathing was connected through a filter 76 to the J valve 70.

Figure 5:
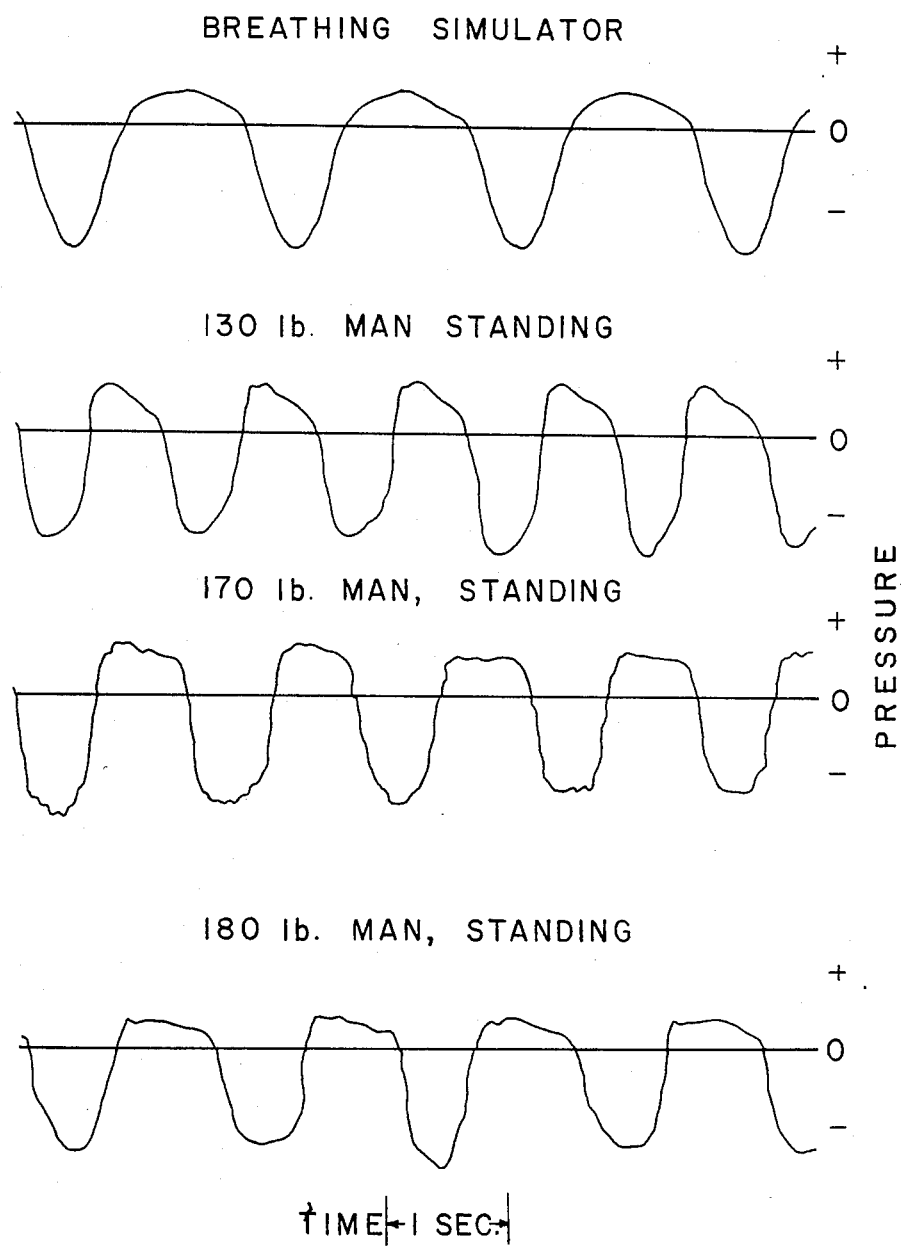
FIG. 5 is a graph relating pressure to time for the respiration of three individuals and the pattern generated by the breathing pump of the present invention.

FIG. 5 shows the pressure variations generated by breathing pump 68 at the top. The respiration of three individuals is also shown in FIG. 5 demonstrating the correlation between the action of the breathing pump 68 and that of actual human breathing. It is noted that only the inhalation (low pressure) stroke is important since this is the stroke which determines how the test gas or vapor is being drawn into the inhalation chamber 64. The scale of pressure is arbitrary but correlated for the four graphs shown in FIG. 5.

Figure 6:
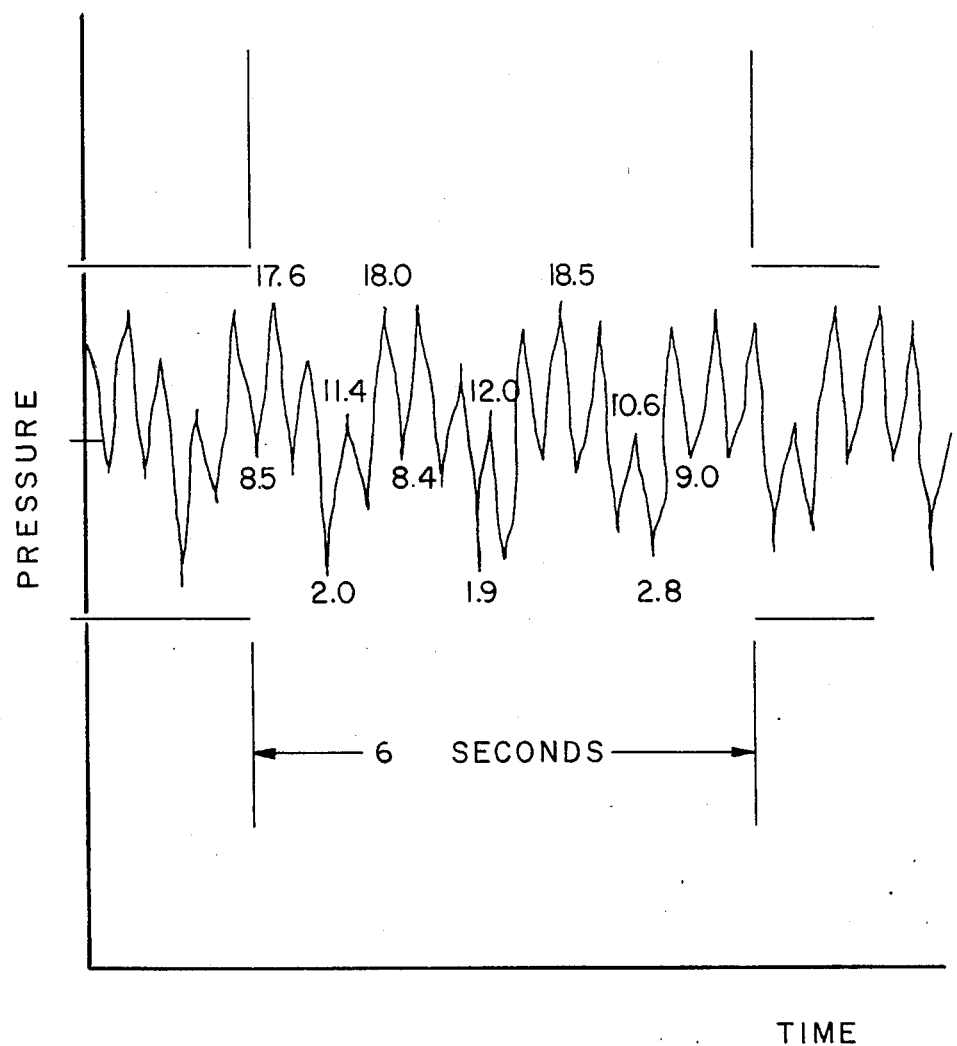
FIG. 6 is a graph relating pressure to time for the respiration of a rat used as a test animal in the present invention.

FIG. 6 shows pressure variations sensed by the plethysmographic equipment 74, indicating the respiratory response for the test animal. Since these pressure variations were superimposed on the pressure variations produced by breathing machine 68, a special technique was utilized to determine tidal volume. Breathing rates are easily taken from the graph shown in FIG. 6. The technique to measure tidal volume utilized the following calculation:

$$\text{Relative Tidal Volume} = \frac{(3 \text{ highest of highs}) - (3 \text{ highest of lows})}{3}$$

$$\text{Relative Tidal Volume} = \frac{(3 \text{ lowest of highs}) - (3 \text{ lowest of lows})}{3}$$

EXAMPLES OF RELATIVE TIDAL VOLUME CALCULATION $$\left. \begin{array}{l} \frac{(17.6 + 18.0 + 18.5) - (8.5 + 8.4 + 9.0)}{3} = 9.4 \\ \frac{(11.4 + 12.0 + 10.6) - (2.0 + 1.9 + 2.8)}{3} = 9.1 \end{array} \right\} 9.2$$

For the various pressure spikes the difference between the three highest of the highs and the three highest of the lows was taken and divided by three. Another value was taken for relative tidal volume which equalled the difference between the three lowest highs and the three lowest lows and this also was divided by three. An average was taken between these two values to determine the tidal volume for the rat at 9.2.

Figure 7:
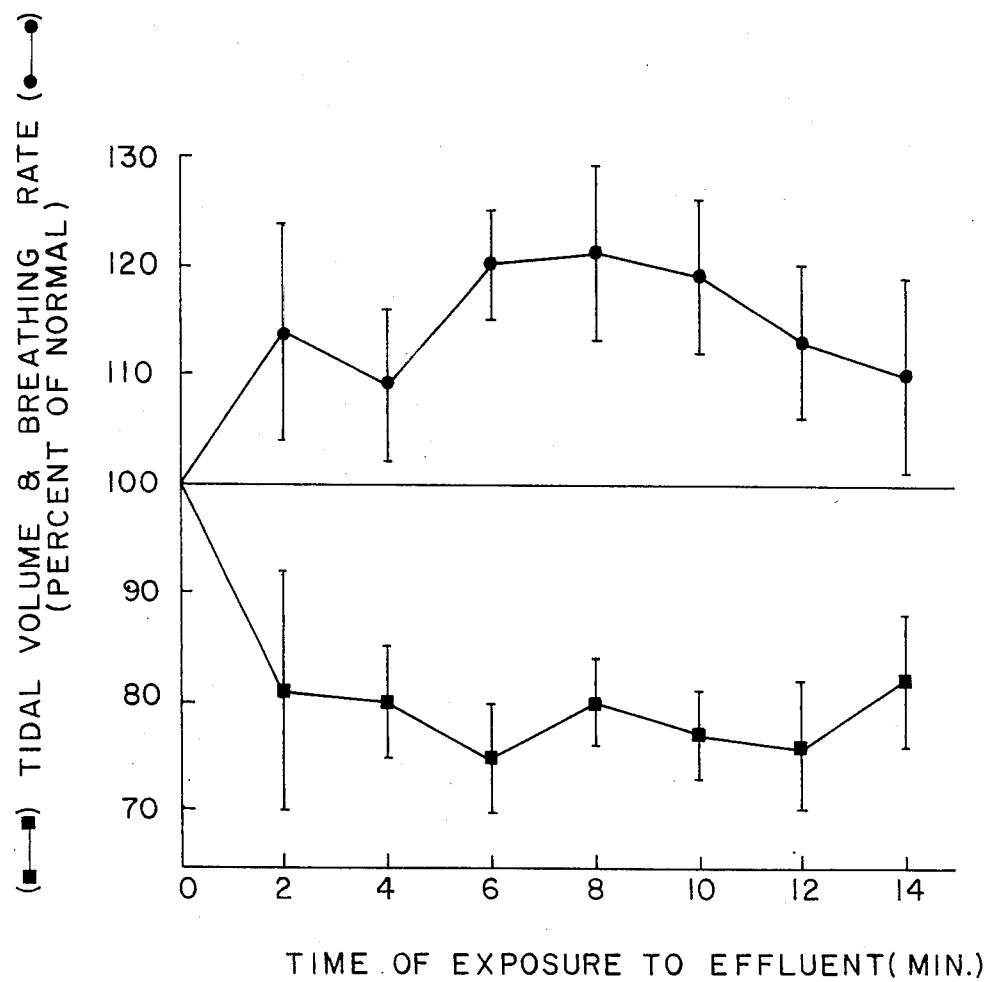
FIG. 7 is a graph relating tidal volume and breathing rate to time for a test animal exposed to the filter element effluent.
Figure 8:
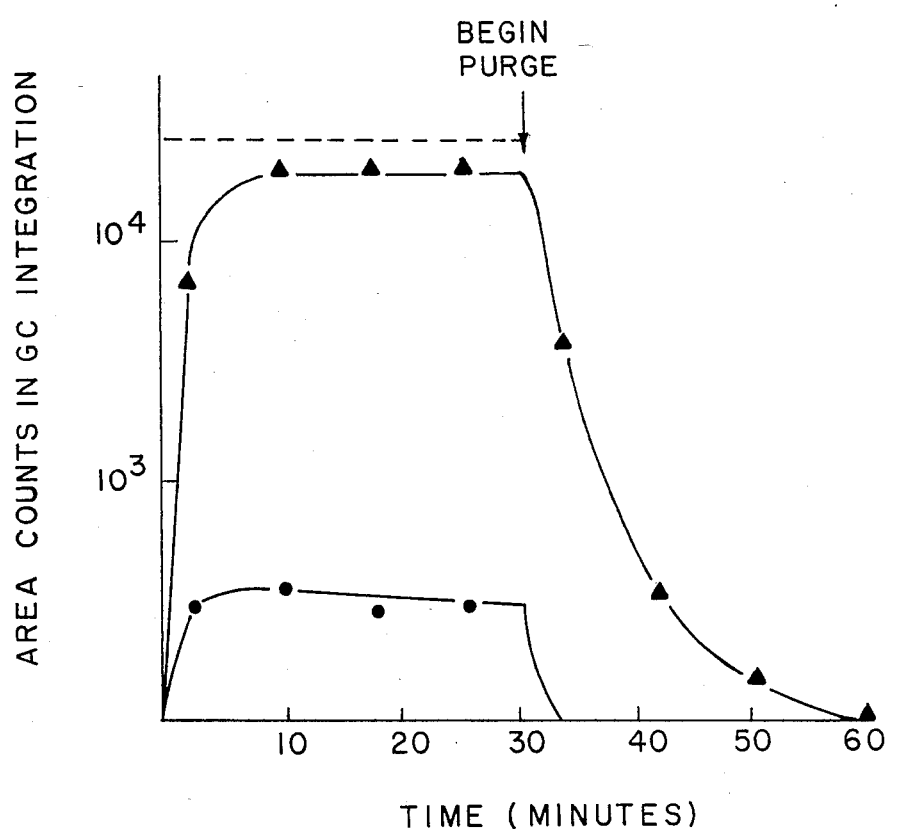
FIG. 8 is a graph showing the results of gas chromatographic analysis for the test gas sample and effluent.

FIG. 7 shows the results for the breathing rate and tidal volume plotted against the time of exposure of the test animals to the effluent. The test animals were exposed to an average flow of 16.0±0.3 liters per minute and the challenge concentration was verified by gas chromatography and/or IR spectroscopy. The respiration data was obtained on the rats for 5 to 10 minutes. At this point the ball valves controlling the test vapor were turned on to begin exposure. Effluent samples were drawn at 5 to 10 minute intervals and the components were characterized and quantitated by the GC or IR methods. Typical exposures consisted of a 30 minute challenge followed by a 30 minute air purge of the filter. After the purge the rats were removed from the plethysmographic boxes and returned to their home cages for observation of toxic signs. FIG. 8 shows the results of the GC analysis.

In reviewing the respiratory response of the rats, it was found that the breathing rates were not proven to be consistent indicators of irritation. A decrease in the relative tidal volume was, however, the most consistent indicator of an irritant in the effluent. This is shown in FIG. 7.

Before initiating the test for each filter element, the filter element was preconditioned to simulate actual field conditions. This involved exposing the test element to a relative humidity of 80±3% and a temperature of 70±5° F. This environment was maintained for approximately 16 hours at a flow rate of 16 liters per minute. Once conditioned the filter was placed in its appropriate filter element box (40 or 41) and the experiment started. Without this prior conditioning the filters would have variable and unrealistic absorption capacities during the test.

The lines entering and leaving the inhalation chamber 64 were selected to be ⅜-inch inside diameter plexiglas tubing with rubber sleeves to reduce pressure variations during maximum flow of the breathing cycle and to more closely approximate actual breathing passages.

While specific embodiments of the invention have been shown and described in detail to illustrate the application of the principles of the invention, it will be understood that the invention may be embodied otherwise without departing from such principles.

What is claimed is:

1. An apparatus for testing a filter for a gas-mask comprising:

a gaseous supply means for supplying a gas sample to a flow system, a box containing a filter in said flow system,
    said box having an inlet and outlet,
    said inlet communicating with said gaseous supply means in said flow system for supplying said gas sample to said filter,
    said outlet for discharging said gas sample to said flow system as an effluent after said gas sample passes through said filter, an inhalation chamber defining a space in said system,
    said inhalation chamber having an inlet and outlet,
    said inhalation chamber inlet communicating with said box outlet in said flow system for supplying said effluent into said space,
    said inhalation chamber outlet for discharging said effluent into said flow system from said space, at least one plethysmographic box connected to said inhalation chamber for receiving a test animal,
    said plethysmographic box having an opening communicating with said inhalation chamber space,
        said opening adapted to receive the head of said test animal, respiration response means connected to said plethysmographic box for measuring said test animal's response, a breathing pump connected to said inhalation chamber outlet,
    said pump drawing said effluent from said inhalation chamber space simulating human respiration, a plurality of test ports for removing a part of said gas sample for chemical analysis,
    said ports provided on said gaseous supply means, said box containing said filter, and said inhalation chamber, a flow-temperature-humidity control unit having an inlet and an outlet,
    said flow-temperature-humidity control unit inlet for admitting clean air, gas metering means communicating between said gas supply means and said box, a mass flow control unit connected between said gas metering means and said flow-temperature-humidity control unit,
    said outlet of said flow-temperature-humidity control unit communicating with said system between said gas metering means and said box,
    said mass flow control unit for controlling the flow of air from said flow-temperature-humidity control unit and the flow of said gas sample from said metering means, and an expandable bag having an opening communicating with said inlet of said box containing said filter.

2. The apparatus of claim 1 wherein a one-way exhaust valve communicates in said flow system between said inhalation chamber and said pump.

3. The apparatus of claim 2 wherein a second filter communicates in said flow system between said one-way exhaust valve and said pump.

4. The apparatus of claim 3 wherein a bidirectional valve utilized for venting is connected between said gas metering means and the flow from said flow-temperature-humidity control unit.

5. The apparatus of claim 4 wherein a bidirectional valve utilized for venting is connected between said box and the flow of said flow-temperature-humidity-control unit.

* * * * *